United States Patent
Padia et al.

(10) Patent No.: US 7,589,217 B2
(45) Date of Patent: Sep. 15, 2009

(54) YIELD IMPROVEMENT IN THE PRODUCTION OF MALEIC ANHYDRIDE

(75) Inventors: Ashok S. Padia, Glen Rock, NJ (US); Howard Sachs, Bronx, NY (US); Martin Millman, Montvale, NJ (US)

(73) Assignee: SD Lizenzverwertungsgesellschaft mbH & Co. KG, Munich (DE)

( * ) Notice: Subject to any disclaimer, the term of this patent is extended or adjusted under 35 U.S.C. 154(b) by 516 days.

(21) Appl. No.: 11/409,791

(22) Filed: Apr. 24, 2006

(65) Prior Publication Data

US 2007/0249848 A1 Oct. 25, 2007

(51) Int. Cl.
*C07D 307/60* (2006.01)

(52) U.S. Cl. ...................... 549/259; 549/260

(58) Field of Classification Search .......... 549/259, 549/260

See application file for complete search history.

(56) References Cited

U.S. PATENT DOCUMENTS

| | | | |
|---|---|---|---|
| 4,649,205 A | 3/1987 | Edwards et al. | 549/260 |
| 5,117,007 A | 5/1992 | Taheri | 549/259 |
| 5,360,916 A | 11/1994 | Padia et al. | 549/259 |
| 5,585,502 A | 12/1996 | Ruggieri et al. | 549/262 |
| 5,688,970 A | 11/1997 | Ruggieri et al. | 549/262 |
| 6,194,587 B1 | 2/2001 | Doshi | 549/258 |
| 6,858,561 B2 | 2/2005 | Bortinger et al. | 502/209 |

*Primary Examiner*—Bernard Dentz
(74) *Attorney, Agent, or Firm*—Scully, Scott, Murphy & Presser, P.C.

(57) ABSTRACT

An improved process for the production of maleic anhydride by the catalytic oxidation of n-butane. Maleic anhydride is produced by reacting n-butane gas with oxygen or an oxygen-containing gas, in the presence of a vanadium phosphorus oxide (VPO) catalyst. An improved yield and selectivity in the production of maleic anhydride is attained by the addition of a substantially pure carbon monoxide gas stream in the reactant feed stream. A process is given for the production of maleic anhydride by reacting a combination of gas streams in the presence of a VPO catalyst. The combination of gas streams comprises an n-butane gas stream, an oxygen or oxygen-containing gas stream, and a substantially pure carbon monoxide gas stream. The amount of carbon monoxide present in the combination of gas streams is from about 0.5 volume % to about 6 volume % based on the total volume of the combination of gas streams.

23 Claims, No Drawings

YIELD IMPROVEMENT IN THE PRODUCTION OF MALEIC ANHYDRIDE

BACKGROUND OF THE INVENTION

1. Field of the Invention

This invention relates to an improved process for the production of maleic anhydride by the catalytic oxidation of n-butane. More particularly, the invention pertains to a process for the production of maleic anhydride by the catalytic oxidation of n-butane having an improved yield and selectivity by the addition of a substantially pure carbon monoxide gas stream in the reactant feed stream.

2. Description of the Related Art

It is well known in the art that maleic anhydride may be manufactured by the vapor phase oxidation of n-butane as it flows through a fixed bed reactor containing a vanadium phosphorus oxide (VPO) catalyst. N-butane in admixture with air is brought into contact with a VPO catalyst under conditions such that the n-butane is oxidized to maleic anhydride. The effluent from the reactor may be cooled to partially condense the product maleic anhydride from the effluent gases. The gaseous product, with or without partial maleic anhydride removal, is scrubbed using a solvent, usually water or an organic solvent, to recover the maleic anhydride. The remaining gases, containing unconverted n-butane, are commonly incinerated in an effluent gas incinerator prior to venting to the atmosphere. Useful processes, as well as VPO catalysts for the production of maleic anhydride from n-butane are known from U.S. Pat. Nos. 6,194,587; 5,360,916 and 6,858,561, which are incorporated herein by reference. U.S. Pat. No. 5,360,916 discloses a two-stage process for maleic anhydride production wherein n-butane is oxidized in a first reaction zone and the effluent from this zone is passed together with supplemental n-butane to a second reactor in series in order to complete production of the maleic anhydride. In U.S. Pat. No. 5,360,916, butane is oxidized with molecular oxygen in a dilute state by bringing a mixture of vaporized butane and air having a controlled butane content into the presence of a vanadium phosphorus oxide catalyst in a first oxidation zone, cooling the gaseous effluent, introducing butane into the cooled gaseous effluent from the first oxidation zone, introducing the cooled butane-enriched stream into the second oxidation zone, and bringing the thus butane-enriched mixture into contact with a vanadium-phosphorus-oxygen catalyst disposed in the second zone. U.S. Pat. No. 6,858,561 teaches a process for preparing a catalyst for maleic anhydride production.

There is a need in the art to improve the selectivity and yield of maleic anhydride production processes. It has now been unexpectedly found that the selectivity and yield of the maleic anhydride production process may be increased by adding a stream of carbon monoxide gas to the inflowing reactant gas streams. This is counter-intuitive. One skilled in the art would presume that the addition of carbon monoxide would tend to reduce selectivity and yield of the maleic anhydride production process.

After recovering the produced maleic anhydride, preferably at least part of the residual gas from the reaction product is then recycled back to the input streams. In the conventional once-through butane oxidation to maleic anhydride process about 80% of the butane is converted to maleic anhydride and by-products. The unconverted butane needs to be disposed of, and is usually burned off as a fuel gas. To improve the yield, i.e., the fraction of butane fed converted to maleic anhydride, the butane can be recycled. In the conventional once-through process, the feed gas is free of carbon monoxide and carbon dioxide reaction by-products, except for a small amount of carbon dioxide which might be contained in the air feed. However, as a consequence of butane recycle the concentration of these by-products will build-up in the recycle gas. In addition, for the recycle process the oxygen concentration can be varied at will, while the once-through process is generally carried out with air and is restricted to 20.9% oxygen. U.S. Pat. No. 5,688,970 teaches a process for the production of maleic anhydride by recycling at least part of the residual gas from the reaction product back to the input streams. However, prior to doing so, the process of U.S. Pat. No. 5,688,970 requires a scrubbing of the residual gases so that only recycled and scrubbed butane re-enters the reaction.

SUMMARY OF THE INVENTION

The invention provides a process for the production of maleic anhydride which comprises reacting a combination of gas streams in the presence of a vanadium phosphorus oxide catalyst; said combination of gas streams comprising an n-butane gas stream, an oxygen or oxygen-containing gas stream and a substantially pure carbon monoxide gas stream, wherein the total amount of carbon monoxide present in the combination of gas streams is from about 0.5 volume % to about 6 volume % based on the total volume of the combination of gas streams, to thereby produce a reaction product comprising maleic anhydride.

The invention also provides a process for the production of maleic anhydride which comprises providing a fixed bed tubular reactor containing a vanadium phosphorus oxide catalyst; continuously flowing a combination of gas streams into the reactor and causing the combination of gas streams to react in the presence of a vanadium phosphorus oxide catalyst within the fixed bed tubular reactor; said combination of gas streams comprising an n-butane gas stream, an oxygen or oxygen-containing gas stream and a substantially pure carbon monoxide gas stream; continuously adding at least one trialkyl phosphite or trialkyl phosphate component to the combination of gas streams in an amount of from about 0.5 ppm to about 4 ppm by weight of elemental phosphorus in the trialkyl phosphate or trialkyl phosphite component, based on the total amount of the combination of gas streams, while applying heat to the combination of gas streams at a temperature of from about 400° C. to about 440° C. and maintaining a maximum temperature of gases present in the combination of gas streams of about 480° C., to thereby produce a reaction product comprising maleic anhydride at a rate of conversion of n-butane to maleic anhydride of about 75% or more.

The invention further provides an improved process for the production of maleic anhydride by reacting a combination of gas streams in the presence of a vanadium phosphorus oxide catalyst; said combination of gas streams comprising an n-butane gas stream, and an oxygen or oxygen-containing gas stream the improvement comprising adding a substantially pure carbon monoxide gas stream to the combination of gas streams, wherein the total amount of carbon monoxide present in the combination of gas streams is from about 0.5 volume % to about 6 volume % based on the total volume of the combination of gas streams, to thereby produce a reaction product comprising maleic anhydride.

DETAILED DESCRIPTION OF THE INVENTION

The oxidation of the n-butane to maleic anhydride may be accomplished by contacting a stream of gaseous n-butane in low concentrations in a stream of oxygen or oxygen containing gas, plus a stream of carbon monoxide gas, with a VPO catalyst in a heated, standard tubular oxidation reactor.

Air is a useful source of oxygen, but mixtures of oxygen and diluent gases, such as nitrogen also may be employed. Air enriched with oxygen may also be used. A gaseous feed stream contains oxygen or an oxygen containing gas such that the amount of oxygen usually ranges in an amount of from about 15 vol % to about 35 vol % based on the total volume of the combination of gas streams, more usually from about 18 vol % to about 30 vol %, and still more usually from about 19 vol % to about 21 vol %.

The gaseous feed stream then contains n-butane such that the amount of n-butane usually ranges in an amount of from about 0.5 vol % to about 3.0 vol % based on the total volume of the combination of gas streams, more usually from about 1.0 vol % to about 2.5 vol %, and still more usually from about 1.5 vol % to about 2.2 vol %. Higher concentrations of n-butane may be employed, provided the amount avoids explosive hazards. Lower concentrations of n-butane, i.e. less than about one mole percent, will reduce the total productivity obtained at equivalent flow rates and thus are not normally economically employed. Diluent gases such as nitrogen may also be incorporated into the feed stream in amounts easily determined by those skilled in the art.

Added to the gaseous feed stream is a substantially pure carbon monoxide gas stream. This carbon monoxide gas stream together with any carbon monoxide attained from a subsequent recycling of reaction residual gases is such that the total amount of carbon monoxide present in the combination of gas streams ranges from about 0.5 volume % to about 6 volume % based on the total volume of the combination of gas streams. A preferred amount is from about 1 volume % to about 5 volume % based on the total volume of the combination of gas streams, and a more preferred amount is from about 2 volume % to about 4 volume % based on the total volume of the combination of gas streams Optionally carbon dioxide is added to the gaseous feed stream. Preferably carbon dioxide, when used is added from a source of substantially pure carbon dioxide. When employed, a useful amount of carbon dioxide usually ranges from about 0.01 volume % to about 5 volume % based on the total volume of the combination of gas streams. A preferred amount is from about 1 volume % to about 4 volume %, and a more preferred amount is from about 2 volume % to about 4 volume % based on the total volume of the combination of gas streams.

Optionally water is added to the gaseous feed stream. When employed, a useful amount of water usually ranges from about 0.5 volume % to about 5 volume % based on the total volume of the combination of gas streams. A preferred amount is from about 1 volume % to about 4 volume %, and a more preferred amount is from about 2 volume % to about 3 volume % based on the total volume of the combination of gas streams Preferably, continuously added to the gas feed stream is at least one trialkyl phosphate or trialkyl phosphite component. Useful trialkyl phosphate or trialkyl phosphite components non-exclusively include trimethyl phosphate, triethyl phosphate, tripropyl phosphate, trimethyl phosphite, triethyl phosphite, and tripropyl phosphite, and combinations thereof. Useful amounts of trialkyl phosphate or trialkyl phosphite component added to the gaseous feed stream is an amount of from about 0.5 ppm to about 4 ppm, preferably from about 1 ppm to about 3 ppm by weight of elemental phosphorus in the trialkyl phosphate or trialkyl phosphite based on the total amount of the combination of gas streams.

A variety of reactors are useful and multiple tube heat exchanger type reactors are satisfactory. The tubes of such reactors may vary in inside diameter from about 0.5 inch (1.27 cm) to about 1.5 inches (3.8 cm), and the length may be varied from about 5 feet (1.524 meters) to about 25 feet (7.62 meters) or more. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be molten sulfur, mercury, molten lead, and the like, but it has been found that eutectic salt baths are most satisfactory. One such salt bath is a sodium nitrate-sodium nitrite-potassium nitrite eutectic mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon steel, nickel, glass tubes such as Vycor and the like which have excellent long life under the conditions for the reactions described herein. Normally, the reactors contain a preheat zone of an inert material such as ¼" Alundum pellets, inert ceramic balls, nickel balls or chips and the like, present at about ½ to $\frac{1}{40}$ the volume of the active catalyst present. The reactors may comprise a single stage, dual sequential stages or multiple sequential stages as described in U.S. Pat. No. 6,194,587. The reactor may be provided with one or more salt circuits along the reactor tubes. Ordinarily, an entire reactor has a single salt circuit maintained at the operating temperature, but it may be desired to have a first temperature zone extending from the inlet of the reactor to any desired downstream point and a second temperature zone extending from that point to the outlet of the reactor.

The catalyst which is suitably used in forming the catalyst beds inside the reactor for carrying out the oxidations can be any of the vanadium phosphorus oxide contact catalysts used in the butane oxidation art and the invention is in no way limited to any particular catalyst. Broadly, the vanadium phosphorus oxide catalysts comprise vanadium, phosphorus and oxygen combined as a complex. The overall ratio of vanadium to phosphorus in the catalyst will have an atomic ratio of about ½ to 3 atoms of phosphorus per atom of vanadium. The vanadium phosphorus oxygen catalyst may also contain various stabilizers and metal additives generally in percents of less than 15 weight percent based on the total weight of vanadium and phosphorus. The atomic ratio of oxygen to the remaining components of the catalyst, when the catalyst is in the process of being used to catalyze the oxidation, is difficult to determine and is probably not constant due to the competing reactions of oxidation and reduction taking place during the reaction at high temperatures. The overall ratio of oxygen to the combined atoms of vanadium and phosphorus at room temperature would be such as about 2 to 6 atoms of oxygen per the combined atoms of vanadium and phosphorus. The catalyst is present during the reaction as an oxide of vanadium and phosphorus. The catalytic material from which the catalyst structure is made is a vanadium-phosphorus-oxygen complex type catalyst for the conversion of hydrocarbons to the corresponding anhydride. The catalyst usually contains at least one modifying component, Me, which is a metal, including the rare earth metals, an alkali metal, an alkaline earth metal, or mixture thereof.

The precise structure of the present complex catalyst has not been determined; however, a preferred complex may be represented by formula $VP_aMe_bO_x$ wherein Me is the modifying component, a is from about 0.90 to about 1.3, b is from about 0.001 or greater, preferably from about 0.005 to about 0.4. The representation is not an empirical formula and has no significance other than representing the atom ratio of the active metal components of the catalyst. The x has no determinate value and can vary widely, depending on the combinations within the complex, and is selected to complete the valence requirements of the complex. Among the various Me components used either alone or in combination with each other are elements which are metal and metaloids from Group Ia, Ib, Ia, IIb, IIIa, IIIb, IVa, IVb, Va, the 4th period of VIIIb, and the rare earths of the Periodic Table of elements. Some specific Me components may be Cu, Ag, Zn, Cd, Al, Ga, In, Sc, Y, La, Ge, Sn, Pb, Ti, Zr, Sb, Bi, As, Fe, Co, Ni, Ce, Pr, Nd, Cr, Li, Na, K, Rb, Fr, Nb, Te, W, Pd, Mn, Mo, Re, Sm, Hf, Ta, Th, U, Sn, B, Si, Mg, Ba, Tb and Eu. More preferred Me components are Cu, Mo, Ni, Co, Cr, Nd, Ce, Ba, Y, Sm, Te, Zr, W, Pd, Ag, Mn, Zn, Re, La, Hf, Ta, Th, U, Eu, Nb, Ru, Li, Mg, B and Si. The Me components may be considered as stabilizers, promoters, modifiers or the like, however, regardless of the characterization the Me components are a part of the catalyst, in that they affect the performance in the oxidation of the n-butane. The activity of the catalyst may be moderated by dispersing 5 to 50% (by volume) discrete inert structures, such as alumina. Particularly advantageous catalysts are those described in U.S. Pat. Nos. 4,251,390; 3,980,585 and 4,105,586. The catalyst may be employed as pellets, disc, flakes, wafers, or any other convenient shape which will facilitate its use in the tubular reactors employed for this type of vapor phase reaction. For example the catalyst may be prepared as tablets having a hole or bore therethrough as disclosed in U.S. Pat. No. 4,283,307. Generally, an unsupported catalyst will have higher surface area than supported catalysts. The final catalyst particle size for this arrangement is usually about 2½ to about 10 Tyler mesh. After activation the surface area is preferably less than 100 m$^2$/g and preferably at least 1 m$^2$/g and more preferably at least 5 m$^2$/g.

The flow rate of the gaseous feed stream through the reactor may be varied within rather wide limits but a useful range of operations is at a gas hourly space velocity (GHSV) of from about 1,000 to about 4,000, preferably from about 1,500 to about 3,000, and more preferably from about 1,600 to about 2,800. Residence times of the gas stream in contact with the catalysts will normally be less than about 4 seconds, more preferably less than about one second, and down to a rate where less efficient operations are obtained. The gaseous feed stream is usually supplied to the reactors at an inlet pressure of from about 0.6 kg/cm$^2$ gauge to about 4.0 kg/cm$^2$ gauge, preferably from about 1.0 kg/cm$^2$ gauge to about 3.0 kg/cm$^2$ gauge, and more preferably from about 1.2 kg/cm$^2$ gauge to about 2.5 kg/cm$^2$ gauge.

The temperature of reaction may be varied, but normally the reaction should be conducted at temperatures within a rather narrow range. The temperature in the reactor will also depend to some extent upon the size of the reactor and the n-butane concentration. The oxidation reaction is exothermic and once reaction is underway, the main purpose of the salt bath or other media is to conduct heat away from the walls of the reactor and control the reaction. The reactors are heated to an outside temperature of from about 380° C. to about 460° C., preferable from about 390° C. to about 450° C., and more preferably from about 400° C. to about 430° C. Under useful operating conditions, the maximum temperature of the gas in the reactor, measured by a thermocouple or other probe, is about 430° C. to about 470° C. This maximum temperature of the gas along the length of the reactor inside the reactor tube is called "hot spot" and generally needs to be controlled to maintain the stability of reaction. It is known to those skilled in the art that since heat is applied to the outside surface of the reactor tubes, and the reaction itself is exothermic, the temperature profile of the gases present in the reaction is not constant across the diameter of the reaction tubes. Since the oxidation reaction is exothermic, once reaction is underway, a main purpose of the salt bath or other media is to conduct heat away from the walls of the reactor and control the reaction. The flow of salt in the circuit is maintained at a rate such that the above-specified temperature values are achieved. The "hot spot" as defined above is generally 30° C. to 60° C. higher than the temperature of the coolant (generally molten eutectic salt). The higher "hot spot" promotes further oxidation of the maleic anhydride product resulting in reduced yield and also causes the deactivation of the catalyst. However, a feature of this invention is that the "hotspot" temperature of gases present in the reaction be maintained at a maximum of about 480° C. or less, preferably about 470° C. or less to minimize the loss of yield and possible deactivation of the catalyst. The added phosphorus component aids in suppressing the hotspot temperature.

The reaction may be conducted at atmospheric or above atmospheric pressure. The exit pressure will be at least slightly higher than the ambient pressure to insure a positive flow from the reactor. The pressure of the gases must be sufficiently high to overcome the pressure drop through the reactor.

After the effluent gas exists the reactor it is cooled to a range of from about 50° C. to about 200° C. range. The exit gas from the reactor after cooling is usually scrubbed in a water bath to remove maleic anhydride as maleic acid or by an organic solvent to remove maleic anhydride as a solute in the organic solvent. The maleic anhydride may be recovered in a number of ways well known to those skilled in the art. For example, the recovery may be by direct condensation or by absorption in suitable media, with subsequent separation and purification of the maleic anhydride.

According to the invention, a conversion of n-butane to maleic anhydride of about 75% or more is achieved, more usually in the range of from about 75% to about 94%, and still more usually from about 80% to about 92%. According to the invention, a selectivity of n-butane to maleic anhydride of about 70 mol % or more is achieved. This more usually in the range of from about 71 mol % to about 76 mol %, and still more usually from about 72 mol % to about 76 mol %. According to the invention, a yield of n-butane to maleic anhydride of about 95 weight % or more is achieved. This more usually in the range of from about 97 weight % to about 103 weight %, and still more usually from about 99 weight % to about 103 weight %.

The following non-limiting examples serve to illustrate the invention.

EXAMPLES

A 1 inch OD by 0.834 inch ID, 17 ft long stainless steel jacketed reactor tube was prepared by filling the jacket with a low melting temperature heat transfer salt which was then heated by electric band heaters strapped to the wall of the jacket. The salt was circulated through a heated external leg by a salt pump for improved heat transfer. A ⅛ inch, thin wall thermowell was put down the center of the tube to measure internal gas temperature. The reactor tube was charged with 15 ft of SynDane® 3122 catalyst commercially available from the Scientific Design Company, Inc. of Little Ferry, N.J. and prepared according to U.S. Pat. No. 6,858,561. Operating conditions are shown below:

TABLE 1

| Conditions: | |
| --- | --- |
| Space velocity | 1850 |
| Inlet pressure | 20 psig |
| Butane inlet concentration | 1.8 vol % |
| Inlet water concentration | 1.7 vol % |
| Conversion target | 80-82% |

TABLE 2

| Variable conditions: | | |
| --- | --- | --- |
| Example | $O_2$ | $CO + CO_2$ |
| 1 | 30 | 0 |
| 2 | 30 | 6 |
| 3 | 20.9 | 6 |
| 4 | 20.9 | 0 |
| 5 | 26 | 3 |

Liquid butane was vaporized and fed to the reactor under flow control. The CO and $CO_2$ were fed as pure gases premixed in a 55/45 ratio that simulated the ratio of CO and $CO_2$ normally encountered and fed to the reactor under flow control. Air and pure oxygen were fed separately under flow control to give the desired oxygen concentration.

The reaction temperature of 395° C. to 405° C. was maintained by controlling the temperature of the salt via the electric heaters to give the desired concentration. Feed and effluent gases were analyzed for butane, CO and $CO_2$ by on-line infrared analyzers. The following results are noted.

TABLE 3

| | Example 1 (*) | Example 2 | Example 3 (**) | Example 4 | Example 5 |
| --- | --- | --- | --- | --- | --- |
| Oxygen (%) | 30.0 | 30.0 | 20.9 | 20.9 | 26 |
| CO (%) | 0 | 3.25 | 0 | 3.25 | 1.65 |
| $CO_2$ (%) | 0 | 2.65 | 0 | 2.65 | 1.35 |
| Salt Temp (° C.) | 395 | 395 | 402 | 402 | 398 |
| Maleic anhydride Selectivity (mol %) | 71.2 | 75.2 | 69.5 | 73.4 | 72.3 |
| Maleic anhydride Yield (wt %) | 97.5 | 102.8 | 95.2 | 100.4 | 98.9 |
| Maleic anhydride Selectivity Improvement (mol %) | — | 4.0 (1) | — | 3.9 (2) | 2.8 (2) |
| Maleic anhydride Yield Improvement (wt %) | — | 5.3 (1) | — | 5.2 (2) | 3.7 (2) |

(*) Example 1 is the reference case for 30% oxygen.
(**) Example 3 is the reference case for 20.9% oxygen
(1) In comparison to reference Example 1
(2) In comparison to reference Example 3

Results (1) Maleic anhydride selectivity and maleic anhydride yield increase with addition of CO in the reactor feed.

(2) Maleic anhydride selectivity and maleic anhydride yield increase by increasing oxygen concentration in the inlet of the reactor (by adding pure oxygen to feed).

Maleic anhydride Selectivity(Mol%)=65.5+0.65×$CO_x$+0.19×$O_2$

Maleic anhydride Yield(Wt%)=89.7+0.89×$CO_x$+0.26×$O_2$

The results of the experiments show that, increasing the oxygen concentration improved the yield and increased catalyst activity. Increasing activity allows lower temperature operation. Adding CO and $CO_2$ to the feed had no effect on activity but a surprisingly positive effect on selectivity. Between 0% and 6%, butane selectivity (mols maleic anhydride formed per mols butane reacted) increased by nearly 4% and weight yield (kgs. maleic anhydride formed per kg butane fed) increased by 5.2-5.3 points.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the production of maleic anhydride, the process comprising reacting a combination of reactant gaseous feed streams in the presence of a vanadium phosphorus oxide catalyst; said combination of reactant gaseous feed streams comprising an n-butane gaseous feed stream, an oxygen or oxygen-containing gaseous feed stream and a substantially pure carbon monoxide gaseous feed stream, wherein the total amount of carbon monoxide present in the combination of reactant gaseous feed streams is from about 0.5 volume % to about 6 volume % based on the total volume of the combination of reactant gaseous feed streams, to thereby produce a reaction product comprising maleic anhydride.

2. The process of claim 1 further comprising subsequently recovering maleic anhydride from the reaction product.

3. The process of claim 1 further comprising subsequently recovering maleic anhydride and a residual gas from the reaction product, and then recycling at least part of the residual gas back to the combination of reactant gaseous feed streams.

4. The process of claim 1 further comprising adding a phosphorus containing compound to the combination of reactant gaseous feed streams.

5. The process of claim 1 further comprising adding at least one trialkyl phosphite or trialkyl phosphate component to the combination of reactant gaseous feed streams.

6. The process of claim 1 further comprising adding at least one of trimethyl phosphate, triethyl phosphate, tripropyl phosphate, trimethyl phosphite, triethyl phosphite, and tripropyl phosphite to the combination of reactant gaseous feed streams.

7. The process of claim 5 wherein the at least one trialkyl phosphite or trialkyl phosphate component is present in an amount of from about 0.5 ppm to about 4 ppm by weight of elemental phosphorus in the trialkyl phosphate or trialkyl phosphite component, based on the total amount of the combination of reactant gaseous feed streams.

8. The process of claim 1 wherein the reacting is conducted while applying heat to the combination of reactant gaseous feed streams at a temperature of from about 400° C. to about 440° C. and maintaining a maximum temperature of gases present in the reaction of about 480° C.

9. The process of claim 1 wherein the oxygen-containing reactant gaseous feed comprises air.

10. The process of claim 1 wherein the reacting is conducted in a fixed bed tubular reactor.

11. The process of claim 1 wherein the oxygen or the oxygen-containing gaseous feed stream is present in the combination of reactant gaseous feed streams such that the amount of oxygen ranges from about 15 volume % to about 35 volume % based on the total volume of the n-butane gaseous feed stream and oxygen or oxygen-containing gaseous feed stream.

12. The process of claim 1 wherein the n-butane gaseous feed stream is present in the combination of reactant gaseous feed streams in an amount of from about 0.5 vol % to about 3.0 vol % based on the total volume of the n-butane gaseous feed stream and oxygen or oxygen-containing gaseous feed stream.

13. The process of claim 1 further comprises a diluent gas in the combination of reactant gaseous feed streams.

14. The process of claim 1 wherein the combination of reactant gaseous feed streams further comprises a diluent gas which comprises nitrogen, carbon dioxide or combinations thereof.

15. The process of claim 1 wherein the combination of reactant gaseous feed streams further comprises a diluent gas which comprises carbon dioxide wherein the carbon dioxide is present in an amount of from about 0.5 vol % to about 6.0 vol % based on the total volume of the combination of reactant gaseous feed streams.

16. The process of claim 1 wherein the vanadium phosphorus oxide catalyst has the formula $VP_aMe_bO_x$ wherein a is from about 0.90 to about 1.3, b is from about 0.001 or greater, x is selected to complete the valence of the catalyst; and Me is an element selected from Group Ia, Ib, Ia, IIb, IIIa, IIIb, IVa, IVb, Va, the 4th period of VIIIb, and the rare earths of the Periodic Table of elements.

17. The process of claim 1 wherein the combination of reactant gaseous feed streams flows through the reactor at a gas hourly space velocity of from about 1,500 to about 3,000.

18. The process of claim 1 wherein the combination of reactant gaseous feed streams has a reaction residence time of about 4 seconds or less.

19. The process of claim 1 wherein the combination of reactant gaseous feed streams has an inflow pressure of from about 0.6 kg/cm$^2$ gauge to about 4.0 kg/cm$^2$ gauge.

20. The process of claim 1 wherein the conversion of n-butane to maleic anhydride is from about 75% to about 94%.

21. A process for the production of maleic anhydride which comprises providing a fixed bed tubular reactor containing a vanadium phosphorus oxide catalyst; continuously flowing a combination of reactant gaseous feed streams into the reactor and causing the combination of gas streams to react in the presence of a vanadium phosphorus oxide catalyst within the fixed bed tubular reactor; said combination of reactant gaseous feed streams comprising an n-butane gas stream, an oxygen or oxygen-containing gas stream and a substantially pure carbon monoxide gas stream; continuously adding at least one trialkyl phosphite or trialkyl phosphate component to the combination of reactant gaseous feed streams in an amount of from about 0.5 ppm to about 4 ppm by weight of elemental phosphorus in the trialkyl phosphate or trialkyl phosphite component, based on the total amount of the combination of gas streams, while applying heat to the combination of gas streams at a temperature of from about 400° C. to about 440° C. and maintaining a maximum temperature of gases present in the combination of gas streams of about 480° C., to thereby produce a reaction product comprising maleic anhydride at a rate of conversion of n-butane to maleic anhydride of about 75% or more.

22. The process of claim 21 further comprising subsequently recovering maleic anhydride from the reaction product.

23. In a process for the production of maleic anhydride by reacting a combination of reactant gaseous feed streams in the presence of a vanadium phosphorus oxide catalyst; said combination of reactant gaseous feed streams comprising an n-butane gas stream, and an oxygen or oxygen-containing gas stream the improvement comprising adding a substantially pure carbon monoxide gas stream to the combination of reactant gaseous feed streams, wherein the total amount of carbon monoxide present in the combination of reactant gaseous feed streams is from about 0.5 volume % to about 6 volume % based on the total volume of the combination of gas streams, to thereby produce a reaction product comprising maleic anhydride.

* * * * *